United States Patent [19]

Spetzler et al.

[11] Patent Number: 5,258,007
[45] Date of Patent: Nov. 2, 1993

[54] POWERED SURGICAL INSTRUMENT

[75] Inventors: Robert F. Spetzler, 6107 N. Palo Cristi, Paradise Valley, Ariz. 85253; Phillip J. Petillo, Ocean, N.J.

[73] Assignee: Robert F. Spetzler, Paradise Valley, Ariz.

[21] Appl. No.: 882,945

[22] Filed: May 14, 1992

[51] Int. Cl.⁵ .............................................. A61B 17/00
[52] U.S. Cl. .................... 606/208; 606/205; 606/206; 606/139; 606/142; 606/138; 227/901
[58] Field of Search ........ 606/138, 139, 142, 205–208; 433/157, 158, 161

[56] References Cited

U.S. PATENT DOCUMENTS

| | | | |
|---|---|---|---|
| H1028 | 3/1992 | Falk et al. | 606/205 |
| 984,756 | 2/1911 | Frisch | 606/207 |
| 2,316,297 | 4/1943 | Southerland et al. | 606/139 |
| 3,613,683 | 10/1969 | Kees, Jr. et al. | |
| 3,814,102 | 6/1974 | Thal | 606/207 |
| 4,038,987 | 8/1977 | Komiya | |
| 4,169,476 | 10/1979 | Hiltebrandt | |
| 4,289,131 | 9/1981 | Mueller | |
| 4,369,788 | 1/1983 | Goald | 606/207 |
| 4,635,638 | 1/1987 | Weintraub et al. | |
| 4,661,309 | 4/1987 | Hayes | 376/248 |
| 4,674,501 | 6/1987 | Greenburg | 606/142 |
| 4,711,482 | 12/1987 | Brown et al. | 294/19.1 |
| 4,997,436 | 3/1991 | Oberlander | 606/142 |

FOREIGN PATENT DOCUMENTS

| | | | |
|---|---|---|---|
| 3048758 | 7/1982 | Fed. Rep. of Germany | 606/205 |
| 2210315 | 6/1989 | United Kingdom | 606/139 |

Primary Examiner—Stephen C. Pellegrino
Assistant Examiner—Jeffrey A. Schmidt
Attorney, Agent, or Firm—Cahill, Sutton & Thomas

[57] ABSTRACT

A remotely controlled, powered applier for attaching aneurism clips has a fixed jaw and a movable jaw at the end of an extension having two parallel rods. Longitudinal motion of a movable rod causes the jaws to open or close. The proximal ends of the rods are connected to an actuator having a radially symmetrical housing. Within the actuator, a movable rod is attached to a rotary to linear motion converter driven by a small, reversible, electric motor. Footswitches control the speed and direction of the motor and the action of the jaws. The rotary to linear converter is an internally threaded sleeve rotated by the motor and engaging a thread on the proximal end of the movable rod.

6 Claims, 2 Drawing Sheets

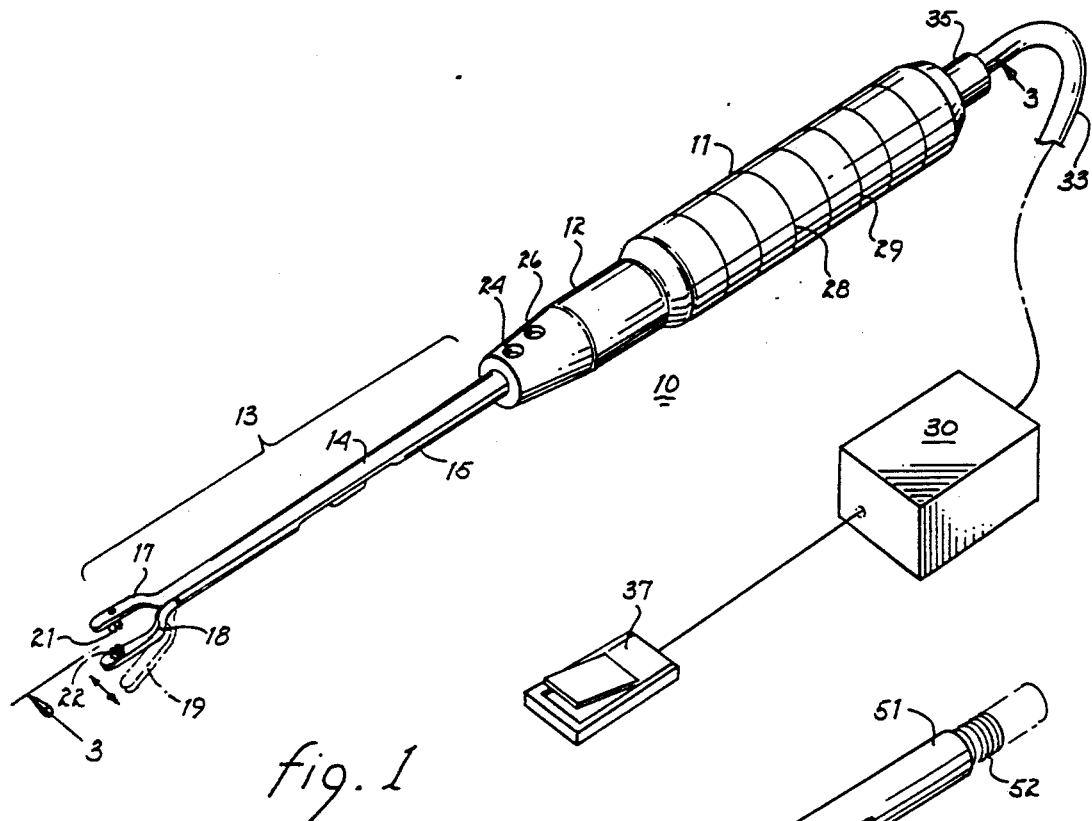
fig. 1
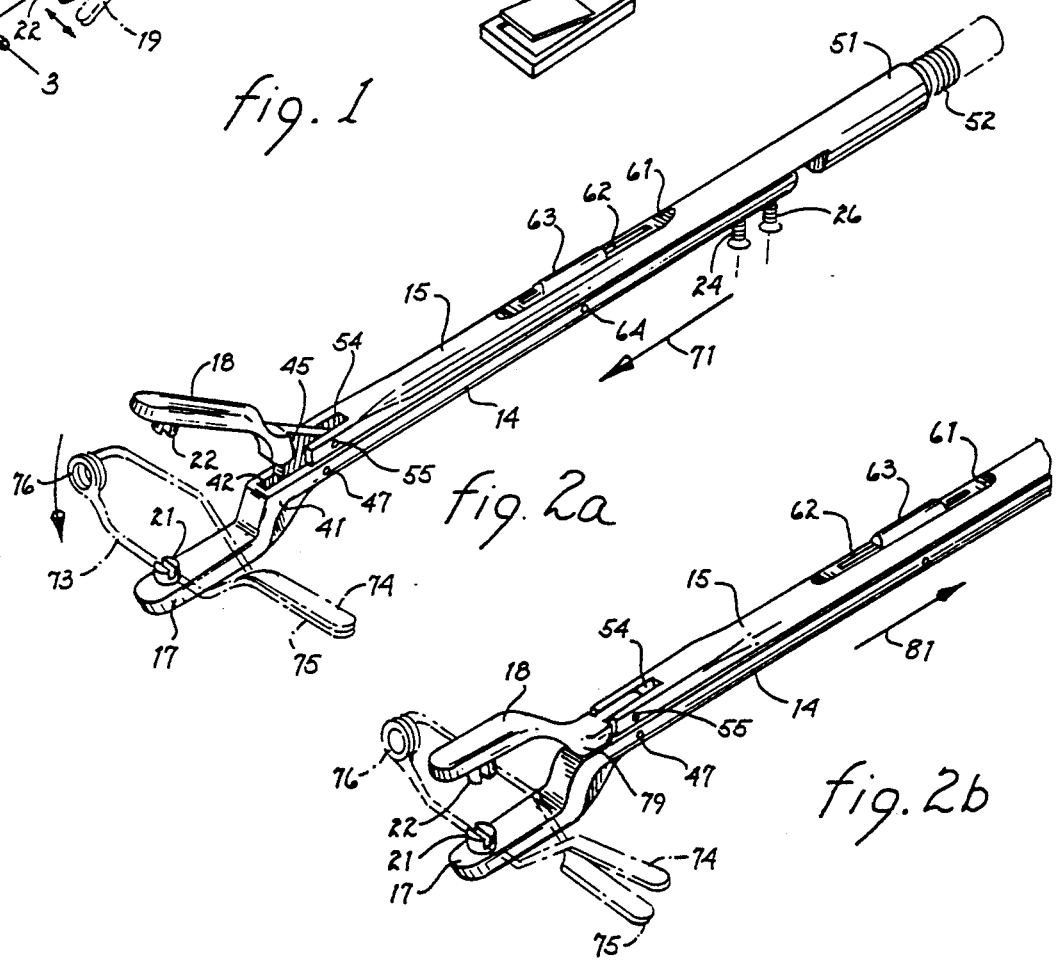
fig. 2a
fig. 2b

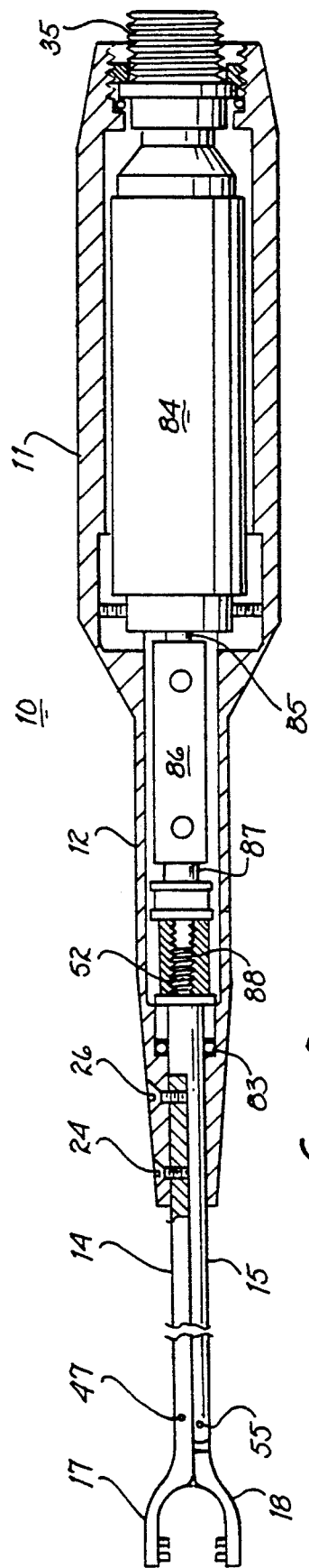
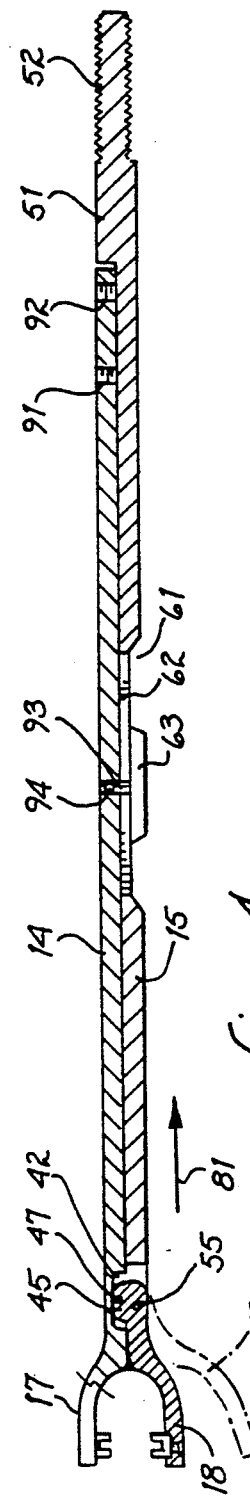
fig. 3
fig. 4

POWERED SURGICAL INSTRUMENT

BACKGROUND OF THE INVENTION

This invention relates to surgical instruments and, in particular, to a powered instrument for attaching and removing a clip on a blood vessel during a surgical operation.

In various surgical operations, it is often necessary to temporarily close blood vessels to prevent loss of blood and to prevent the surgeon's view from becoming obscured by blood. In some procedures, a hemostat (a forceps-like instrument) is used to press together opposite sides of a blood vessel to block the flow of blood. The hemostat has a latch mechanism on its handles for keeping the jaws of the hemostat closed upon the blood vessel until the latch is released by the surgeon. For deep incisions, there is often not enough room for one or more hemostats to be left in place while the procedure continues. In this situation, spring loaded clamps, known as aneurism clips, are used which are much smaller than a hemostat and interfere much less with the surgeon. The clips are attached and released with a separate instrument known as an applier.

Aneurism clips are well known in the art and are commercially available in over one hundred sizes and shapes to meet every possible circumstance which a surgeon may encounter. The problem is getting the clip to the attachment site properly oriented with respect to the vein or artery. A second, but no less significant problem, is to apply the clip with an instrument which does not obscure the surgeon's view of the site or of adjacent, delicate tissue.

Minimally invasive surgical procedures, i.e. procedures using the smallest and fewest incisions possible, were originally used for surgery in and around the brain. Later, arthroscopic surgery was developed. Now, minimally invasive procedures are being developed for all areas of the body, e.g. abdominal and thoracic surgery. Any minimally invasive procedure greatly increases the skill required of the surgeon since the exposure of the patient is small. When a small incision is combined with a deep exposure, e.g. 100 mm, visualization and application can become quite difficult.

At rest, a clip is held closed by a spring which is an integral part of the clip. For insertion, the clip is placed in the jaws of the applier and is opened by closing the jaws of the applier. Clip appliers of the prior art are typically articulated or hinged at a point near one end, i.e. the jaws are much shorter than the handles. Since the jaws of the applier are closed, the handles of the applier are relatively close to each other. In this position, the applier is as narrow as it can be.

Positioning the clip can be difficult if it is necessary to insert the applier in a direction other than perpendicular to the surface of the body. Even though the jaws are closed, the width of the applier limits its insertion angle, i.e. the angle from perpendicular. In addition, the surgeon must rotate his hand to orient the clip properly with respect to the blood vessel. Often, this obliges the surgeon to operate the applier at an awkward hand position.

Opening the jaws of the applier to attach the clip, or to retrieve the clip, can be quite difficult because this widens the applier. Since the hinge is near one end of the applier, the handles must be opened a considerably greater distance than the jaws open. It becomes progressively more difficult to operate the applier at greater depths. The applier can obscure the surgeon's view of the clip and the blood vessel, particularly at the critical moment of attachment or removal. Both jaws move in commercially available appliers, requiring a clear view of both jaws and the region around them. In addition, the surgeon must manually actuate the applier without letting the hand motion cause any other movement of the applier. The result is a time consuming, delicate process which prolongs the surgery and is very demanding of the surgeon.

U.S. Pat. No. 3,613,683 discloses a clip applier using a pair of parallel bars sliding one on the other, actuated by the gripping action of the surgeon's hand. One end of the fixed bar is in the shape of a hook for receiving a clip, which is held between the ends of the two bars. While providing a somewhat narrower instrument, it requires the surgeon to rotate his hand to orient the clip and to manually operate the instrument.

U.S Pat. No. 4,038,987 discloses a forceps used as a clip applier having jaws operated by a toggle joint connected by wire to a syringe-like actuator. As with other appliers in the prior art, the surgeon must rotate his hand to orient the clip and manually operate the instrument.

In view of the foregoing, it is therefore an object of the invention to provide a powered, remotely controlled, surgical instrument for operating a jaw mechanism at any desired rotational orientation relative to the hand of a surgeon.

A further object of the invention is to provide an aneurism clip applier which can be oriented prior to insertion.

Another object of the invention is to provide an aneurism clip applier which requires no separate hand movement for attaching or removing clips from blood vessels.

A further object of the invention is to provide a surgical instrument capable of greater insertion angle than prior art instruments.

Another object of the invention is to provide an aneurism clip applier enabling improved visualization and application.

SUMMARY OF THE INVENTION

The invention achieves the foregoing objects in an applier having a fixed jaw and a movable jaw at the end of an extension. The extension includes two parallel rods, each rod having a semi-elliptical cross-section with the flat sides of the rods facing each other. A movable jaw is attached to the ends of both rods by two pins. The pin attached to the fixed rod serves as a pivot pin, while the pin attached to the movable rod serves as a coupling pin. Longitudinal relative motion of the rods causes the jaws to open or close. The fixed rod is attached to the housing of an actuator. Within the actuator, the movable rod is attached to a rotary to linear motion converter driven by a small, reversible, electric motor. The movable rod does not rotate but is moved longitudinally along the fixed rod to operate the jaws. The housing of the actuator holds together the proximal ends of the rods. In addition, the rods are attached to each other by a sliding fastener positioned near the midpoint of their length to prevent the rods from buckling apart. The housing is radially symmetrical so that the jaws can be oriented in any direction in the surgeon's hand. The motor is controlled by a foot switches to control the direction and speed of the motor and the action of the jaws. The rotary to linear converter is an internally threaded sleeve rotated by the motor and engaging a thread on the proximal end of the movable rod. A clutch is included between the motor and the movable rod.

A more complete understanding of the invention can be obtained by considering the following detailed description in conjunction with the accompanying drawings, in which:

FIG. 1 illustrates an applier, and its power supply, constructed in accordance with a preferred embodiment of the invention.

FIG. 2a is a more detailed illustration of the extension portion of the applier with the jaws in an open position.

FIG. 2b illustrates the closure of the jaws of the extension.

FIG. 3 is a longitudinal cross-section of the actuator for the jaws.

FIG. 4 is a longitudinal cross-section of the extension.

DETAILED DESCRIPTION OF INVENTION

In FIG. 1, applier 10 has two main components: an actuator in a housing including handle 11 and collar 12, and extension 13. Handle 11 contains a reversible electric motor controlled by power supply 30 and footswitches 37 and 38. Collar 12 is attached to handle 13 and encloses a portion of one end of extension 13, herein referred to as the proximal end. Collar 12 provides a transition or taper between handle 11 and extension 13.

Extension 13 includes parallel rods 14 and 15 having jaws 17 and 18, respectively, at the distal ends thereof, i.e. the ends remote from collar 12. Rods 14 and 15 each have a semi circular or semi elliptical cross section with the longitudinal flat surface of one rod facing the longitudinal flat surface of the other rod. Thus, extension 13 has a slender, cylindrical or pencil shape.

The proximal end of rod 14 is attached to collar 12 so that it cannot move longitudinally relative to handle 11 or collar 12. Jaw 17 is attached to the end of rod 14 and is preferably formed from the distal end of rod 14 so that it is integral with rod 14. This construction is stronger than if jaw 17 were a separate piece. Jaw 18 is pivotally attached to the distal end of rod 15, as more fully described in connection with FIGS. 2a and 2b. Jaw 18 opens to position 19 for receiving a clip. Sockets 21 and 22 are attached to the interior faces of jaws 17 and 18, respectively, for holding a clip.

Rod 14 is attached to collar 12 by way of screws 24 and 26. Rod 15 is longitudinally movable into and out of collar 12, for opening and closing jaw 18. Handle 11 is round or some other radially symmetrical shape so that the jaws can be oriented in any direction, yet the handle has the same feel to the surgeon. The outer surface of handle 11 is relatively smooth with light texturing, indicated by Shallow grooves 28 and 29, for providing a secure grip for the gloved hand of the surgeon.

Handle 11 encloses a small, reversible, electric motor coupled to a circular to linear motion converter. Power for the motor is provided by power supply 30 connected to handle 11 by cord 33 and connector 35. Connector 35 also serves as a strain relief, preventing cord 33 from becoming kinked at the point where it enters handle 11. Power supply 30 can be any suitable means for providing power to the motor in handle 11. For example, in one embodiment of the invention, power supply 30 is a variable voltage, direct current (D.C.) power supply. Footswitches 37 and 38 control the magnitude and polarity of the voltage applied to the motor.

Actuating footswitch 37 causes the motor to rotate in one direction, closing the jaws, while actuating footswitch 38 causes the motor to rotate in the opposite direction, opening the jaws. Suitable electric motors are commercially available and typically include some form of gear reduction to reduce the output speed to a suitable level, e.g. 3-15 revolutions per minute (rpm). For example, one embodiment of the invention uses a motor sold by Micromo Inc.

FIGS. 2a and 4 illustrate extension 13 in greater detail. In FIG. 2a, the rods and jaws are upside down relative to the illustration of FIG. 1. Screws 24 and 26 engage threaded bores 91 and 92 (FIG. 4) in the proximal end of rod 14, attaching it to collar 12. The distal end of rod 14 is bent and shaped to form jaw 17. Adjacent bend 41, channel 42 is formed in rod 14 for receiving web 45 of movable jaw 18. Pin 47 extends through rod 14 and web 45 to secure jaw 18 to fixed rod 14. Pin 47 serves as a pivot pin for jaw 18.

Proximal end 51 of rod 15 extends past the end of rod 14 and has a circular cross section, threaded as indicated at 52. The distal end of rod 15 has channel 54 formed therein to produce a forked end which straddles web 45 of movable jaw 18. The forked end of rod 15 is attached to web 45 by pin 55. Pin 55 is a coupling pin between movable rod 15 and movable jaw 18.

As described thus far, rods 14 and 15 are connected at one end by movable jaw 18 and are enclosed at the other end by collar 12. Rods 14 and 15 can be made as long as necessary for the particular application. Because of the force applied to the rods, it is preferred that the rods be attached to each other every two to three inches to prevent rod 15 from buckling as it is compressed longitudinally to close jaw 18, or to prevent rod 14 from buckling as it is compressed longitudinally to open jaw 18. Thus, for an extension six inches long, the rods need only be additionally attached at their midpoints.

The fastener for attaching rods 14 and 15 to each other is preferably a T-shaped fitting, as shown in FIGS. 2a and 4. Recess 61 is formed in the outer surface of rod 15, i.e. opposite the flat side. Within the recess, channel 62 extends through rod 15. Into this channel, T-shaped fitting 63 is inserted with stem 93 (FIG. 4) of the T extending into bore 94 in rod 14. Pin 64 extends through rod 14 and the stem of fitting 63 to attach fitting 63 to rod 14. The arms of fitting 63 extend along rod 15 above recess 61 and are wider than channel 62 to provide a large contact area with recess 61. Fitting 63 is fixed and rod 15 slides back and forth underneath the arms of the T.

The fastener does not increase the thickness of the extension and, while closely fitting, does not impair the movement of rod 15. It does not matter which orientation the fastener has. That is, the fastener could ride in a recess in rod 14 with the stem of the T in rod 15.

FIGS. 2a, 2b, and 3 illustrate the geometry of movable jaw 18. In FIG. 2a, showing jaw 18 in an open position, rod 15 is in a withdrawn position, i.e. moved to the right, and pivot pin 47 is located slightly closer to the distal end of rod 14 than coupling pin 55. When rod 15 is moved in the direction indicated by arrow 71, jaw 18 is rapidly closed toward jaw 17 because pins 47 and 55 are relatively close together. At the same time, because coupling pin 55 is attached to pivot pin 47 by web 45, coupling pin 55 orbits pin 47 and the end of rod 15 is separated from the end of rod 14, i.e. the flat surfaces no longer touch. The flexure of rods 14 and 15 is minimal. When the jaws are closed, FIGS. 2b and 3, coupling pin 55 is closer than pin 47 to the distal end of rod 14 and the ends of the rods again touch each other.

In FIGS. 2a and 2b, aneurism clip 73 has jaws 74 and 75 held closed by integral spring 76. The jaws and spring are interconnected by a wire and configured such that jaws 74 and 75 open as jaws 17 and 18 close. The wire portion of clip 73 fits within grooves in sockets 21 and 22, securely holding clip 73. Although sockets 21 and 22 can rotate to orient clip 73, the applier must also be rotated about the longitudinal axis of extension 13 to place clip 73 on the blood vessel correctly. This can now be done prior to insertion, i.e. outside the patient. The surgeon need not twist his hand because the handle is radially symmetrical.

FIG. 2b illustrates jaws 17 and 18 in a closed position, with rod 15 extending from collar 12 and knee 79 resting against rod 14. In the closed position, jaws 17 and 18 squeeze the wires of clip 73, opening in jaws 74 and 75, as illustrated. In order to release clip 73, rod 15 is moved in the direction of arrow 81, causing jaw 18 to pivot about pin 47 and open. Jaws 74 and 75 are closed by spring 76.

FIG. 3 illustrates the mechanical connections within handle 11 and collar 12 for extending and retracting rod 15. Elements in common with other FIGURES have the same reference numerals as in the other FIGURES. Within handle 11, electric motor 84 is preferably a reversible D.C. motor with suitable gearing to reduce the speed of output shaft 85. In one embodiment of the invention, a DC motor having an operating speed of 25,000 rpm is reduced to six rpm.

The rotary motion of output shaft 85 is coupled by coupling 86 through clutch 87 to internally threaded sleeve 88. The primary function of sleeve 88 is to convert rotary motion to linear motion. Threads 52 of rod 15 are screwed part way into sleeve 88. As motor 84 turns sleeve 88 one way or the other, threads 52 are drawn into or pushed out of sleeve 88. The jaws close before threads 52 come all of the way out of sleeve 88. Rod 15 does not rotate since it is connected to rod 14 and rod 14 is secured to collar 12 by screws 24 and 26. Thrust bearings, not shown, prevent sleeve 88 from moving longitudinally within collar 12. O-ring 83 seals the end of collar 12 about the round portion of rod 15. 0-ring 89 seals the other end of handle 11.

Sleeve 88 performs a second function in that it adapts the actuator for different extensions. One simply removes screws 24 and 26, unscrews the extension from sleeve 88, and then screws in an extension of a different length or purpose. Threaded bores 91 and 92 (FIG. 4) in rod 14 provide alignment marks for inserting the extension into the collar. That is, one cannot over- or under-insert an extension since the screw holes in the collar will not line up with bores 91 and 92. Thus, an extension can only be screwed into sleeve 88 to the proper depth for screws 24 and 25 to fit. Sleeve 88 performs a third function in that it locks jaw 18 in any desired position. When sleeve 88 stops, it is not possible to apply a force on jaw 18 which could cause sleeve 88 to rotate. If sleeve 88 does not rotate, the jaw can not move. The surgeon is thus relieved of the task of precisely holding the jaws at a certain position manually. In addition, unlike hemostats and other instruments of the prior art, the locked position is continuously variable rather than incrementally variable. Also, the locked position is bidirectional, i.e. the jaws can be used to pry and hold apart as well as to clamp shut. Thus, an applier constructed in accordance with the invention gives a surgeon greater precision and functionality than has been available previously.

Because of the gear reduction in the motor and the further mechanical advantage from the motion converter, the force available on rods 14 and 15 can be considerable, in excess of seventy pounds. In one embodiment of the invention, extension 13 has an elliptical cross-section, with the flat sides of rods 14 and 15 on the minor axis (shorter diameter) of the ellipse. The ellipse has a minor axis of 0.125 inches and a major axis of 0.188 inches. Although made from 316 alloy stainless steel and only four inches from the collar to the tip of the jaws, the extension included the T-shaped fitting described above to prevent buckling.

The force available on the rods is not necessary for the particular use of attaching and removing aneurism clips. With different jaws, the applier of the invention can be adapted to many other uses, for example as forceps, for cutting, for clamping e.g. a needle, for punching or puncturing, and for bipolarizing (sealing blood vessels by electric cautery).

The extension has an additional advantage in that all surfaces of the extension are easily exposed to steam or other sterilant. Even the small space between the opposed flat surfaces is easily penetrated by sterilant since the rods are narrow. Alternatively, the rods can be separated slightly for cleaning or sterilizing.

The human hand can grasp an object in two basic ways. One way is a power grip, as one would use for holding a hammer. The other way is a precision grip, as one would use for holding a pencil. An applier constructed in accordance with the invention can be held either way. In the embodiment referred to above, the handle has an outside diameter of 0.750 inches, which is a comfortable size for a power grip. The applier can also be held by the collar like a pencil, with the handle resting on the outside of the hand between the thumb and forefinger. Since a clip applier does not need to produce large forces, a smaller motor could be used to make the handle smaller for a precision grip its entire length.

The invention provides a compact, powerful, comfortable, precision instrument for the surgeon. Because of the slender extension, the insertion angle can vary considerably, within the limits of the geometry of the exposure. The surgeon's view is improved because of the small cross-section of the extension and because the bulk of the instrument is outside the patient at all times. Application is much easier because it does not require a separate motion of the hand to attach or release the clips and the clips can be oriented prior to insertion. Also, the applier can be used in either hand since it is radially symmetrical.

Having thus described the invention, it will be apparent to those of skill in the art that various modifications can be made within the scope of the invention. For example, depending upon use, both jaws can be separate from the rods and attached to the rods with a hinge. Any suitable escapement or frictional, viscous, or magnetic clutch can be used to prevent excessive force on the jaws. Alternatively, a resilient coupling can be used between the rod and the motor to limit the amount of force which can be transmitted; e.g. coupling 86 could comprise a rubber tube which simply twists out of shape under excessive torque. A reversible alternating current (A.C.) motor, and A.C. power supply, can be used instead of the D.C. motor and power supply described. Instead of or in addition to a clutch or escapement, one can use cushioned stops in the housing to prevent excessive motion of the rods. Since the motion of rod 15 is linear, one can easily add suitable transducers and electronics to provide audible, visual, or tactile feedback to indicate how much force is being applied by the jaws or when a predetermined force is reached or to limit the force automatically by stopping the motor. Instead of two parallel rods, an alternative embodiment of the invention used a concentric rod and cylinder. An advantage of the concentric rod and cylinder is that the buckling is minimized since the forces are concentric. Disadvantages were that, although functional, the extension was difficult to clean, lubricate, and assemble. The extension can be made from any material suitable for the intended use. Other alloys or even composite or plastic materials can be used, if they can be sterilized.

We claim:
1. A powered surgical instrument comprising:
 a first jaw and a second jaw;
 a pivot pin interconnecting said first jaw and said second jaw;
 a reversible electric motor having a rotating output shaft;
 conversion means connected to said shaft for converting rotary motion to linear motion;
 first and second parallel rods, each having a proximal end and a distal end, wherein said first jaw is attached to the distal end of said first rod;
 a housing enclosing said electric motor, said conversion means, and the proximal ends of said first and second rods;
 wherein the proximal end of said first rod is connected to said housing and the proximal end of said second rod is connected to said conversion means for longitudinally moving said second rod;
 a coupling pin connecting the distal end of said second rod to said second jaw so that longitudinal relative motion of said rods opens or closes said jaws; and
 control means electrically connected to said motor for selectively applying power to said motor for actuating said jaws.
2. The instrument as set forth in claim 1 wherein said control means includes a foot switch.
3. The instrument as set forth in claim 1 wherein said housing is radially symmetrical.
4. The instrument as set forth in claim 1 wherein the proximal end of said second rod is threaded and said conversion means is an internally threaded sleeve coupled to said output shaft and partially surrounding the threaded end of said second rod.
5. An instrument for attaching and removing a clip on a blood vessel during a surgical operation comprising:
 a housing;
 first and second parallel rods, each having a proximal end within said housing and a distal end, a longitudinal flat surface, and a semi-elliptical cross-section in which said flat surface intersects the minor axis of said ellipse;
 wherein said flat surfaces face each other and said second rod has a recess in the outer surface thereof and a channel in said recess extending through said second rod;
 a T-shaped fitting having the stem of the T attached to said first rod and the arms of said T extending along said second rod above said channel and in said recess
 first and second jaws interconnected by a pivot pin, wherein said first jaw is attached to the distal end of said first rod;
 a coupling pin connecting the distal end of said second rod to said second jaw so that longitudinal relative motion of said rods opens or closes said jaws;
 actuating means contained within said housing for longitudinally moving one rod relative to the other.
6. The instrument as set forth in claim 5 wherein said rods are held together at said proximal ends by said housing and wherein said first rod is attached to said housing.

* * * * *